(12) United States Patent
Blanche et al.

(10) Patent No.: US 6,537,793 B2
(45) Date of Patent: Mar. 25, 2003

(54) METHOD OF SEPARATING VIRAL PARTICLES

(75) Inventors: Francis Blanche, Paris (FR); Anne Barbot, Verrieres-les-Buisson (FR); Beatrice Cameron, Paris (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/883,451

(22) Filed: Jun. 14, 2001

(65) Prior Publication Data

US 2002/0037565 A1 Mar. 28, 2002

Related U.S. Application Data

(63) Continuation of application No. PCT/FR99/03315, filed on Dec. 30, 1999.
(60) Provisional application No. 60/119,948, filed on Feb. 12, 1999.

(30) Foreign Application Priority Data

Dec. 31, 1998 (FR) .............................................. 98 16737

(51) Int. Cl.$^7$ .............................. C12N 7/02; C12Q 1/00
(52) U.S. Cl. ................................ 435/239; 435/4; 435/5; 210/634; 210/638; 210/656; 210/660
(58) Field of Search ............................... 435/4, 5, 239; 210/634, 638, 656, 660

(56) References Cited

U.S. PATENT DOCUMENTS 5,591,440 A * 1/1997 Carman et al. .......... 424/227.1

FOREIGN PATENT DOCUMENTS

| WO | WO 96/27677 A2 | 9/1996 |
|----|----------------|--------|
| WO | WO 97/08298 A1 | 3/1997 |
| WO | WO 98/00524 A1 | 1/1998 |
| WO | WO 98/22588 A2 | 5/1998 |
| WO | WO 98/39467 A2 | 9/1998 |

OTHER PUBLICATIONS

Haruna, Ichiro et al., Separation of Adenovirus by Chromatography on DEAE–Cellulose, Virology, vol. 13, 1961, pp. 264–267.

Huyghe, Bernard G et al., Purification of a Type 5 Recombinant Adenovirus Encoding Human p53 by Column Chromatography, Human Gene Therapy, vol. 6, Nov. 1995, pp. 1403–1416.

Klemperer, H G et al., Study of Adenovirus Antigens Fractionated by Chromatography on DEAE–Cellulose, Virology, vol. 9, 1959, pp. 536–545.

Shabram, Paul W et al., Analytical Anion–Exchange HPLC of Recombinant Type–5 Adenoviral Particles, Human Gene Therapy vol. 8, Mar. 1, 1997, pp. 453–465.

* cited by examiner

Primary Examiner—Hankyel T. Park
Assistant Examiner—Stacy S. Brown
(74) Attorney, Agent, or Firm—Finnegan, Henderson, Farabow, Garrett & Dunner, L.L.P.

(57) ABSTRACT

The invention concerns a novel method for purifying and quantifying viral particles. More particularly, the invention concerns a method for purifying and quantifying adenovirus by ion-exchange chromatography. The invention also concerns a method for identifying different adenovirus serotypes.

14 Claims, 6 Drawing Sheets

METHOD OF SEPARATING VIRAL PARTICLES

The present invention relates to a new method for the purification and quantification of viral particles. More particularly, the invention relates to a method of purifying and quantifying adenoviruses by ion-exchange chromatography. The invention also relates to a method of identifying various adenovirus serotypes.

Gene therapy is currently undergoing a remarkable development and various clinical studies in humans have been in progress since the first trials conducted in 1990. Among the methods commonly used for the transfer of genes, viral vectors have proved particularly promising, and adenoviruses occupy a key position among them.

The development of adenovirus vectors in gene therapy requires access to two types of technologies which are nowadays limiting for the production of viral stocks: the first is to have a method which is rapid, is highly sensitive and is very selective for the quantification of viral particles in samples obtained from the steps of constructing and amplifying the virus considered; this point is particularly important for the optimization of the method of producing viral stocks; the second is to have a method of purification which is reliable, reproducible, simple and can be easily extrapolated on the industrial scale for the purification of virus particles.

The production of clinical batches of adenoviruses remains a long procedure because of the number of transfection and amplification steps whose productivity is not optimized. Recombinant adenoviruses are usually produced by introducing viral DNA into an encapsidation line, followed by mechanical or chemical lysis of the cells after about two or three days of culture (the kinetics of the adenoviral cycle being from 24 to 36 hours). According to another variant, the culture is continued for a longer period (8 to 12 days), and the viruses are directly harvested in the supernatant after spontaneous release by a phenomenon of autolysis of the encapsidation cells (WO 98/00524).

Generally, between 2 and 7 amplification cycles are necessary to constitute the viral stocks. A major limitation to the optimization of the method of producing viral stocks lies in the methods of titrating the viral particles. Indeed, biological methods are methods which are relatively sensitive and accurate, but are particularly long to carry out (about 4 to 15 days depending on the assay used, i.e. transgene activity (tdu) or plaque production (pfu)). Faster analytical methods have been developed but they do not have a sufficient degree of precision and sensitivity when the titrations of viral particles have to be carried out, without prior purification, in lysates, crude cellular extracts or culture supernatants. That is why successive amplification cycles are carried out with multiplicities of infection (MOI) which are estimated roughly. The result is that the amplification steps are not very reproducible, or are even sometimes longer and/or more numerous than would be necessary with an optimized method. The rapid and precise determination of the titres of adenovirus solutions would make it possible to adjust the multiplicity of infection for each step so as to optimize the entire method of producing adenovirus stocks.

The method of quantifying viral particles should satisfy several conditions. In the first place, it should be sufficiently sensitive to allow the assay of viral particles in preparations which are dilute or which have a low titre (typically $<1\times10^9$ viral particles per ml (vp/ml)) without resorting to a prior enrichment step. It should be possible to carry out the assay of the viral particles directly in lysates or crude preparations, without the need to carry out a purification step or a prior treatment. Furthermore, this method should allow a high selectivity in order to eliminate possible interference with the numerous compounds present in the crude cellular lysates or extracts and of which the proportions may vary depending on the culture conditions.

A quantitative analytical method based on anion-exchange chromatography has been described in the literature (Huygue et al., Human Gene Ther. 6: 1403–1416, 1995; P. W. Shabram et al., Human Gene Ther. 8: 453–465, 1997). This method, which has a detection limit of the order of $1\times10^8$ vp/ml, is applicable to the titration of purified viral particles. However, the sensitivity of this method decreases once the analysis is carried out on lysates or crude cellular extracts. The detection limit is estimated at 2 to $5\times10^9$ vp/ml in such samples and this method does not make it possible to quantify the adenoviral particles in very dilute and nonpurified preparations such as the lysates of cells infected during the virus transfection and amplification steps for which the adenoviral titre is typically of the order of $1\times10^8$ vp/ml to $1\times10^9$ vp/mi. Furthermore, neither does this method make it possible to quantify the adenoviral particles from preparations obtained in certain production media free of animal proteins. Indeed, such media contain, at the end of culture, compounds of the sugar, amino acid, vitamin or phenol red type, and the like, among which some may interfere with the adenoviral particles during the quantification of the virus and which lead to the titre of the preparation being very widely overestimated. Finally, the chromatographic method reported by Shabram et al. requires a pretreatment of the sample with a nuclease with a broad activity spectrum (BENZONASE) in order to remove the nucleic acids which interfere with the detection and measurement of the particles.

As regards the preparative methods of separating adenoviruses, chromatography has been used for many years for the purification of adenoviral particles [Haruna, I., Yaosi, H., Kono, R. and Watanabe, I. *Virology* (1961) 13. 264–267; Klemperer, H. G. and Pereira, H. G. *Virology* (1959) 9, 536–545; Philipson, L., *Virology* (1960) 10, 459–465]. Methods describing the large-scale purification of recombinant adenoviruses have been described more recently (international patent applications WO 96/27677, WO 97/08298, WO 98/00524, WO 98/22588).

Application WO 98/00524 describes in particular a method of purification using the strong anion-exchange resin Source 15Q which makes it possible to obtain, in a single chromatographic step, adenovirus preparations whose purity is at least equivalent to that obtained from preparations purified by caesium chloride gradient ultracentrifugation. This degree of purity is very high and reaches the standards required for clinical studies in humans (WHO Expert Committee on Biological Standardization, Forty-ninth Report. WHO Technical Report Series, WHO Geneva, in press).

However, when the viral titre of the preparations to be purified is low (for example in the case of an adenovirus having a low productivity, or when the purification has to be carried out using a stock obtained during an early amplification step), or alternatively when the virus production medium leads to the presence of compounds co-eluted with the adenovirus (as for example in the case of media free of calf serum), the limited performance of the chromatographic techniques previously described do not make it possible either to quantify or to purify the adenoviral particles in a single step from such a starting material.

The problem of being able to have a method of titrating viral particles from crude preparations which is rapid, sensitive and highly selective therefore exists. The problem of having a method of purification which is reliable, reproducible and makes it possible to obtain, from these same crude preparations, and preferably in a single step, viral preparations of pharmaceutical quality, also exists.

It has now been found, and this constitutes the subject of the present invention, that certain chromatography supports surprisingly exhibit quite exceptional properties for the separation of viral particles and in particular adenoviruses. These properties allow the titration and/or purification of viral particles from crude preparations, with no prior treatment, with a very high sensitivity and selectivity. The use of these supports provides, in addition and unexpectedly, a simple and rapid analytical method for separating and identifying, by chromatography, adenoviruses of different serotypes or adenoviruses modified at the level of the fibre or the hexon.

The subject of the present invention is a method of separating viral particles from a biological medium, characterized in that it comprises at least one chromatography step carried out on a support comprising a matrix and ion-exchange groups, the said groups being grafted onto the said matrix by means of a flexible arm.

The matrix may be chosen from agarose, dextran, acrylamide, silica and poly[styrene-divinylbenzene], alone or in the form of a mixture. Preferably, the matrix consists of agarose; still more preferably, it is approximately 6% cross-linked agarose.

The supports consisting of cross-linked agarose beads onto which are grafted functionalized, flexible ion-exchange arms have been developed for preparative and industrial chromatography of biomolecules. These supports have been more particularly designed for the step of capturing (that is to say the initial step of the method of purification) biomolecules from crude mixtures which have been simply clarified, that is to say freed of their solid constituents in suspension. Their performance was optimized in terms of a very high capacity for attachment of solutes to the support, of a very low counterpressure at a high linear liquid flow rate, of a low cost as well as of a very high chemical resistance to the cleaning agents used for regeneration.

Advantageously, the flexible arm is of a hydrophilic nature and it consists of a polymer of synthetic or natural origin. Among the polymers of synthetic origin, there may be mentioned the polymers consisting of monomers of polyvinyl alcohols, polyacrylamides, polymethacrylamides or polyvinyl ethers.

By way of polymer of natural origin, there may be mentioned in particular polymers of a polysaccharide nature chosen from starch, cellulose, dextran and agarose. Preferably, the degree of polymerization of the flexible arm is about 30 monomeric units, more preferably, the flexible arm is a dextran having a mean molecular weight of about 5000 Da.

Preferably, the flexible arm is functionalized by grafting a group capable of interacting with an anionic molecule. Most generally, the group consists of an amine which may be ternary or quaternary. Within the framework of the present invention, it is particularly advantageous to use a strong anion exchanger. Thus, a chromatography support as indicated above, functionalized by quaternary amines, is preferably used according to the invention.

By way of a support which is particularly preferred for carrying out the invention, there may be mentioned Q SEPHAROSE (Amersham Pharmacia Biotech). The use of this support is mentioned in one of the examples of application WO 98/39467. Purified adenoviruses are modified by treatment with polyethylene glycol (PEG). After reaction, the modified adenoviruses, the unmodified adenoviruses and the PEG are separated by passing over a Q SEPHAROSE XL column. This is therefore a simple separation between the starting materials and the final products of a chemical reaction. Persons skilled in the art could not assume that this column could be used successfully for the separation of adenoviruses from a complex biological medium containing various contaminating species (DNA from the host, RNAs, proteins, lipids, lipoproteins, endotoxins and the like), such as a lysate of encapsidation cells. Neither does it appear on reading this document that Q SEPHAROSE XL can be used for preparative purposes because it is known that the majority of supports lose their efficiency once large quantities of products are injected.

Other strong anion exchange supports having similar characteristics including matrix composition, particle size distribution, porosity, chemical nature of the flexible arm and grafting density may be used for the preparative or analytical separation of adenoviral particles. Advantageously, the matrix consists of 6% cross-linked agarose; it is grafted with flexible arms which consist of dextran and are functionalized with strong anion-exchange groups. The support has a particle size preferably of between about 40 and 200 $\mu$m; the term "about" relating to the particle size means that the value to be taken into consideration is within a deviation of between +/−20% relative to the value expressed. Preferably, this deviation is between +/−10% and more preferably it is between +/−5% relative to the value expressed.

In the most particularly preferred manner, the particle size is between 45 and 165 $\mu$m and is centred on 90 $\mu$m.

Also advantageously, the matrix has a dispersion such that 95% of the particles have a diameter of between 0.1 and 10 times the mean diameter of the particles, and preferably between 0.3 and 3 times the mean diameter of the particles.

The Q SEPHAROSE XL used in the examples which follow illustrates nonexhaustively the performance of the supports which can be used within the framework of the invention.

Figure 1:
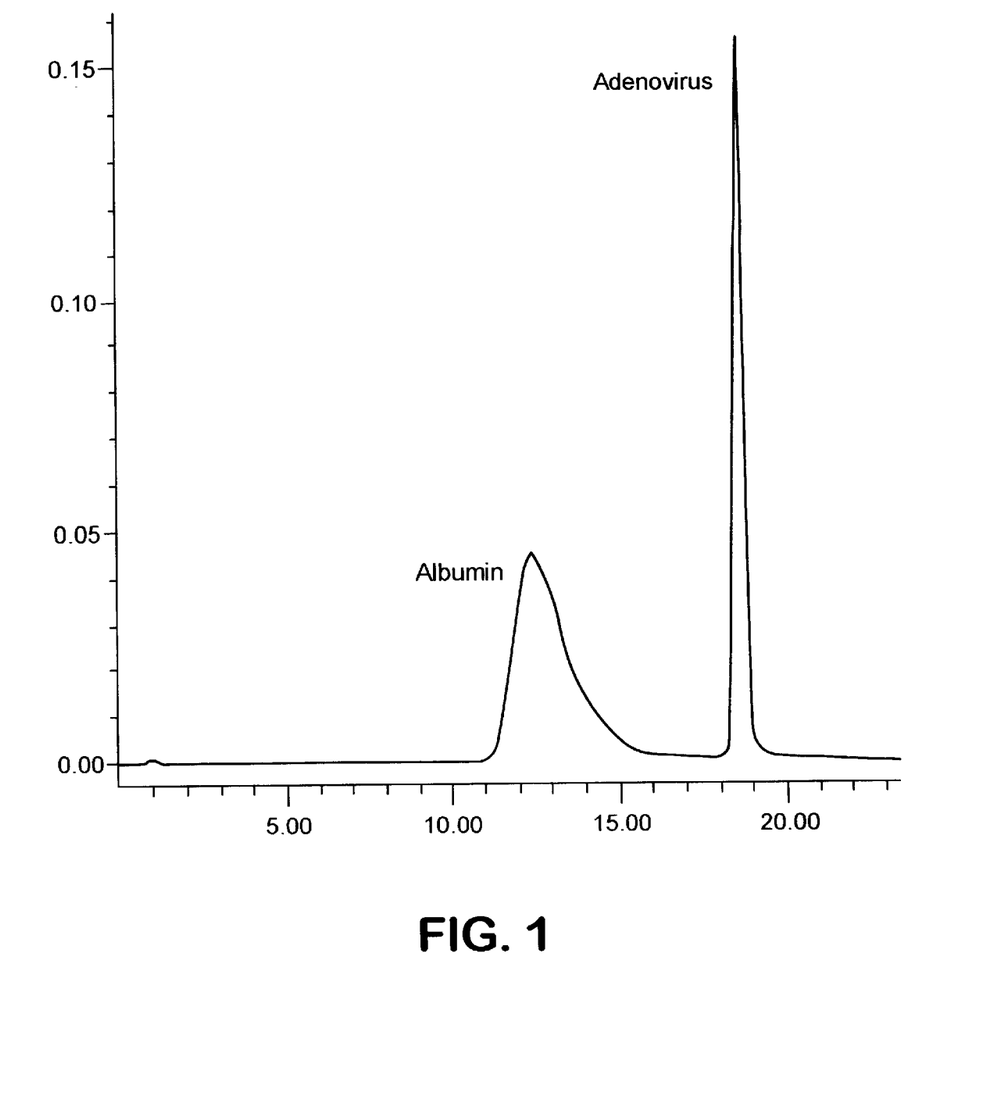
FIG. 1: Elution profile for purified adenovirus and for bovine albumin on Q SEPHAROSE XL.

The Q SEPHAROSE XL exhibits a bead size distribution ranging from 45 to 165 $\mu$m, centred on 90 $\mu$m. These size and bead distribution characteristics make the support a preparative-type chromatographic exchanger. Chromatographic theory and practice indicate that such a support has a very modest performance for the separation of compounds exhibiting similar chromatographic behaviour as regards the ion-exchange interaction. Likewise, such a support generates poorly resolved broad chromatographic peaks, in particular because of the large size and the very wide distribution of the beads constituting it. These expected chromatographic characteristics are verified for biomolecules in general such as proteins, which are eluted in the form of large, poorly separated peaks (see Data File Pharmacia Biotech No. 18-1123-82). On the other hand, in a completely unexpected manner, the adenovirus particles are eluted from this type of support in the form of a very symmetrical, extremely narrow peak. Compared with proteins, such as for example albumin, the efficiency of a column filled with Q SEPHAROSE XL, measured by the Height Equivalent to a Theoretical Plate (HETP) or the number of theoretical plates per unit of column length (N/m), is 50 to 100 times higher for adenovirus (N/m:35,000) than for proteins such as bovine serum albumin (N/m 600). See for example FIG. 1. Thus, when it is used under optimized chromatographic conditions, this type of gel, and in particular the Q SEPHAROSE Sepharose® XL gel, gives an adenovirus chromatographic peak whose narrowness is not equalled by the supports generally recommended for the separation of biomolecules. Among the supports recommended for the separation of biomolecules, there may be mentioned the supports whose basic matrix is of the poly [styrene-divinylbenzene] type (such as for example the resins Source 15Q and Source 30Q, or the resins of the Poros HQ, Poros DE2 or Poros D type). There may also be mentioned supports whose basic matrix is of the methacrylate-ethylene glycol copolymer type such as for example the resins Toyopearl DEAE, QAE and Super Q, or the resins of the Fractogel TMAE, TMAE HiCap, DMAE or DEAE type whose functional ion-exchange groups are situated on polyacrylamide-type linear polymeric chains grafted onto the matrix.

The efficiency of the supports used within the framework of the present invention for the separation of adenovirus particles leads to a very high sensitivity in the detection of the particles. Thus, when these supports are used in analytical chromatographic columns, the unexpected chromatographic behaviour of the viral particles makes it possible to quantify the adenovirus with a detection limit which is way below the detection limit of the methods previously described. This detection limit is at least ten times less than what makes it possible to achieve a detection limit of the order of $1\times10^8$ vp/ml in preparations of the crude cell lysate type and a detection limit of the order of $1\times10^7$ vp/ml for purified viral preparations.

This type of support also makes it possible to provide a very high selectivity towards the contaminants present in the samples to be analysed, such as for example proteins and nucleic acids. The proteins exist in the form of peaks which are very broad and which are eluted way before the viral peak. The nucleic acids are eluted from the column with a saline concentration which is substantially greater than the concentration necessary for the elution of the virus. This characteristic, which is very different from that obtained with the chromatographic method previously described (Huygue et al., Human Gene Ther. 6: 1403–1416, 1995) makes it possible to eliminate interference from this type of compounds with the viral peak. Finally, even when the preparations to be analysed contain species which are co-eluted with the viral particles, the highly specific form of the viral peak makes it possible to easily identify it and to carry out its quantification.

Figure 2:
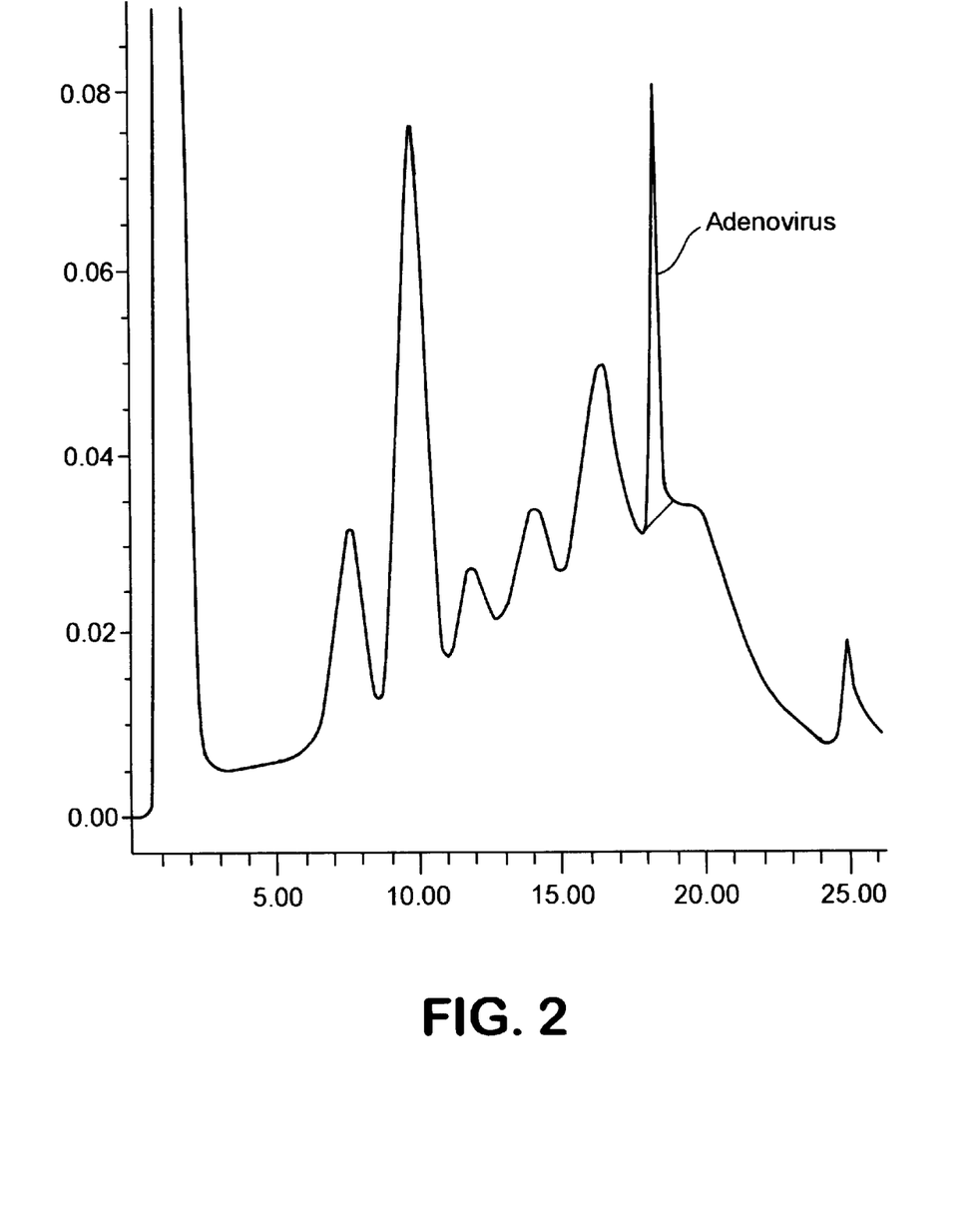
FIG. 2: Elution profile on Q SEPHAROSE for a supernatant of viral culture obtained on a serum-free medium.

Thus, the supports used within the framework of the invention make it possible to identify and quantify very easily and with great accuracy the peak for the adenovirus when the latter is analysed using preparations containing a large quantity of proteins and nucleic acids. The quantitative analysis of the particles as well as the purification can also be carried out using preparations obtained with a wide variety of viral production media or with media free of constituents of animal origin, such as for example albumin, whether of bovine origin, human origin or yet another origin (FIG. 2). It is also important to observe that the method described in the present invention is applicable to the analysis of samples containing nucleic acids without prior treatment with a nuclease without affecting either the sensitivity or the selectivity of the method.

In this regard, another subject of the invention relates to the use of this type of support, and of Q SEPHAROSE XL in particular, for the preparative separation or the purification of viral particles, in particular adenoviruses, from biological media. Such a method of separation may optionally comprise a preliminary chromatography step on another support such as those used in the method which is the subject of application WO 98/00524, and in particular the resin Source 15Q. Such a preliminary step may prove advantageous in specific cases, for example if an excessively large quantity of contaminants is present in the biological medium.

Another subject of the invention relates to the use of this type of support, and of Q SEPHAROSE XL in particular, for the quantitative analysis or the titration of viral particles, in particular adenoviruses, from biological media.

The biological medium from which the purification or titration of the virus is carried out may be a supernatant of encapsidation cells producing the virus or a lysate of encapsidation cells, or a prepurified solution of the said virus. When the preparative separation or the purification of the viral particles is carried out using a supernatant of producing encapsidation cells or a lysate, it may be advantageous to carry out a preliminary ultrafiltration step; preferably this step is carried out by tangential ultrafiltration on a membrane having a cut-off of between 300 and 500 kDa.

The method of purification according to the invention makes it possible to obtain viral preparations of a high quality in terms of purity with high particle yields (of the order of 75 to 80%) in one step, using a stock which is dilute and/or very rich in contaminants, under production conditions which are fully compatible with industrial requirements and with regulations regarding the production of therapeutic molecules.

Another subject of the invention relates to a method of quantifying adenoviruses, characterized in that the viral particles are separated by chromatography on a Q SEPHAROSE XL type support and the quantity of adenovirus is determined by measuring the absorbance of the chromatographic fractions. The method of the invention allows an easier and more accurate monitoring of the kinetics of production, directly on homogeneous samples of supernatant, without pretreatment, which allows a better reproducibility and a better control of the methods of producing the stocks of viral particles.

The subject of the invention is also the use of a Q Sepharose® XL type chromatography support for the identification of various adenovirus serotypes. Indeed, and surprisingly, it has been observed that this type of support makes it possible to separate and identify, simply and rapidly, a wide variety of adenoviruses of various serotypes directly from a sample of viral production medium by determining the retention time and the ratio of the absorbance values at 260 nm and at 280 nm for the chromatographic peak.

As regards the use of chromatography supports within the framework of the present invention, the separation of viral particles for analytical or preparative purposes may be carried out by applying to the chromatography column a salt elution gradient or alternatively according to an isocratic mode, that is to say at constant saline concentration.

For the preparative methods, the chromatographic support may be used in a conventional type chromatography column or in a column suitable for high-performance chromatography systems, using for example the Q SEPHAROSE XL support, or alternatively in an expanded or so-called "fluidizied bed" system, using for example the STREAMLINE Q XL support. The size of the chromatographic column is determined as a function of the quantity of virus present in the starting material.

The viral preparation to be purified may be applied to the support in a buffer whose conductivity is such that the virus is not retained on the support whereas the nucleic acids are bound. Advantageously, the conductivity is adjusted to 45 mS/cm. This specific embodiment then makes it possible to separate, by simple filtration through the Q SEPHAROSE XL support, the virus from the nucleic acids obtained from the host cell contaminating the viral preparation.

The methods of assaying and purifying and characterizing the various serotypes described in the present invention can be applied to various types of viruses, and adenoviruses in particular, whether they are wild-type viruses or recombinant viruses carrying a transgene of interest.

In addition to the above features, the present invention also comprises other characteristics and advantages which will emerge from the following examples which are given by way of illustration and with no limitation being implied.

MATERIALS AND METHODS

1-Adenoviruses and Production of Replication-defective Recombinant Adenoviruses

The adenoviruses are linear, double-stranded DNA viruses of about 36 kilobases in size. Their genome comprises in particular an inverted terminal repeat (ITR) at each end, an encapsidation sequence (Psi), early genes and late genes. The principal early genes are contained in the E1, E2, E3 and E4 regions. Among these, the genes contained in the E1 region in particular are necessary for viral propagation. The principal late genes are contained in the L1 to L5 regions. The Ad5 adenovirus genome has been completed sequenced and is accessible on database (see especially Genebank M73260). Likewise, portions or even the totality of other adenoviral genomes (Ad2, Ad7, Ad12 and the like) have also been sequenced.

For their use in gene therapy, various vectors derived from adenoviruses have been prepared, incorporating various therapeutic genes. In each of these constructs, the adenovirus was modified so as to make it incapable of replicating in the infected cell. Thus, the constructs described in the prior art are adenoviruses being deleted for the E1 region, which is essential for the viral replication, into which heterologous DNA sequences are inserted (Levrero et al., Gene 101 (1991) 195; Gosh-Choudhury et al., Gene 50(1986) 161). Moreover, to improve the properties of the vector, it has been proposed to create other deletions or modifications in the adenovirus genome. Thus, a heat-sensitive point mutation was introduced into the ts125 mutant, making it possible to inactivate the 72 kDa DNA binding protein (DBP) (Van der Vliet et al., 1975). Other vectors comprise a deletion of another region which is essential for viral replication and/or propagation, the E4 region. The E4 region is indeed involved in the regulation of the expression of the late genes, in the stability of the late nuclear RNAs, in the extinction of the expression of the proteins of the host cell and in the efficiency of the replication of the viral DNA. Adenoviral vectors in which the E1 and E4 regions have been deleted therefore possess a transcription background noise and a very reduced viral gene expression. Such vectors have been described for example in applications WO 94/28152, WO 95/02697, WO 96/22378). In addition, vectors carrying a modification in the IVa2 gene have also been described (WO 96/10088).

The recombinant adenoviruses described in the literature are produced from various adenovirus serotypes. Various adenovirus serotypes indeed exist whose structure and properties vary somewhat, but which exhibit a comparable genetic organization. More particularly, the recombinant adenoviruses may be of human or animal origin. As regards the adenoviruses of human origin, there may be preferably mentioned those classified in group C, in particular the type 2 (Ad2), 5 (Ad5) adenoviruses; in group B, the type 7 (Ad7) adenoviruses; or in group A, the type 12 (Ad12) adenoviruses. Among the various adenoviruses of animal origin, there may be preferably mentioned the adenoviruses of canine origin, and in particular all the CAV2 adenovirus strains [Manhattan or A26/61 strain (ATCC VR-800) for example]. Other adenoviruses of animal origin are cited in particular in application WO 94/26914 incorporated into the present application by reference.

In a preferred embodiment of the invention, the recombinant adenovirus is a group C human adenovirus. More preferably, it is an Ad2 or Ad5 adenovirus.

Several methods have been described for the generation of recombinant adenoviruses (C. Chartier et al., J. Virol. 70: 4805–4810, 1996; WO 96/25506; J. Crouzet et al., Proc. Natl. Acad. Sci USA 94: 1414–1419, 1997; T-C. He et al., Proc. Natl. Acad. Sci. USA 95: 2509–2514, 1998). These methods make it possible to construct in E. coli plasmids carrying the adenoviral genome of interest; these plasmids are then digested with a restriction enzyme in order to excise the adenoviral genome from the plasmid. The adenoviral genome is then transfected into an encapsidation line and then amplified.

The recombinant adenoviruses are usually produced by introducing viral DNA into the encapsidation line, followed by lysis of the cells after about 2 or 3 days (the kinetics of the adenoviral cycle being 24 to 36 hours); according to another variant, the culture is continued up to 8 to 12 days and the viral particles are spontaneously released into the culture medium by autolysis of the encapsidation cells.

The viruses used within the framework of the examples which follow are adenoviruses containing the lacZ marker gene of E. coli ($AV_{1.0}$CMV.lacZ). These viruses are derived from the Ad5 serotype and possess the following structure:

a deletion in the E1 region covering for example nucleotides 386 (HinfI site) to 3446 (Sau3a site).

a cassette of expression of the lacZ gene, under the control of the CMV promoter, inserted at the level of the said deletion.

a deletion of the E3 region.

The construction of these viruses has been described in the literature (WO 94/25073, WO 95/14102, WO 96/25506, J. Crouzet et al., Proc. Natl. Acad. Sci USA 94: 1414–1419, 1997). It is understood that any other construct may be used in the method according to the invention, and in particular viruses carrying other heterologous genes and/or other deletions (E1/E4 or E1/E2 for example).

The techniques for transfection of the cells, amplification and titration of the adenoviruses have been described previously (F. L. Graham et al., Molecular Biotechnology 3: 207–220, 1995; Crouzet et al., Proc. Natl. Acad. Sci USA 94: 1414–1419, 1997; WO 96/25506).

The tdu technique for assaying the β-galactosidase activity encoded by the lacZ gene contained in the $AV_{1.0}$CMV.lacZ viruses is performed as described by P. Yeh et al (J. Virol. 70: 559–565, 1996).

Production of the $AV_{1.0}$CMV.lacZ Adenoviruses

The virus was harvested from the cultures of produced lines by a conventional method involving a series of freeze-thaw cycles, or by chemical lysis in the presence of 1% Tween-20, or by continuing the culture until autolysis is obtained according to the method described in WO 98/00524.

The culture media may vary depending on the transcomplementing lines used or according to the quantities used. These media may be MEM, DMEM and the like, supplemented or otherwise with calf serum and containing various concentrations of inorganic salts, sugar, amino acids, vitamins, herpes or phenol red.

The E1 region transcomplementing cells such as the cells 293 or PER.C6 are transfected at 60–80% confluence in a culture dish with a viral DNA obtained by digesting a plasmid carrying the adenoviral genome of interest. The incubation lasts for 8 to 15 days, the time of harvest is determined by microscope observation of the cells which become round, become more refringent and adhere increasingly weakly to the culture support. The virus is then released from the nucleus by 3 to 6 successive thaw cycles (ethanol-dry ice at −70° C. water bath at 37° C.). The virus thus obtained is used to infect new transcomplementing cells at a given multiplicity of infection (MOI) which may vary between 10 and 500 viral particles per cell, the amplified virus is obtained as above by continuing the incubation from 40 to 72 h.

According to another variant described in application WO 98/00524, the cells are not harvested 40 to 72 hours post-infection, but the incubation is prolonged between 8 to 12 days so as to obtain complete lysis of the cells without the need to carry out freeze-thaw cycles. The virus is then spontaneously released into the supernatant. The supernatant is then clarified by filtration on depth filters of decreasing porosity (10 μm/1.0 μm/0.8–0.2 μm). The clarified supernatant is then concentrated by tangential ultrafiltration on a Millipore spiral membrane having a cut-off of 300 kDa. The concentration factor is of the order of 20 to 100 fold. According to another variant, the clarified supernatant may be used as it is for the purification of the adenoviral particles by chromatography on a Q SEPHAROSE XL column.

Analysis of the Adenovirus Preparations

The various analytical techniques used for determining the quality of the viral preparations obtained (SDS-PAGE, Western blot analysis, IE-HPLC on Resource 15Q column and the like) have previously been described (WO 98/00524).

2- Analytical Methods Using the Q SEPHAROSE XL Chromatography Support

The operating conditions for the detection, identification and quantification of the adenovirus particles from a culture of infected encapsidation cells are obtained as described below.

A chromatography column filled with about 1 ml of Q SEPHAROSE XL (45–165 μm; Amersham-Pharmacia Biotech) is prepared in a type HR 5/5 column (Amersham-Pharmacia Biotech). This column is mounted on a Waters 626 type HPLC system equipped with a UV/visible detection system with a diode array 996 operating in the 200–300 nm absorbance range. This anion-exchange column is used for the separation and quantification of the viral particles.

Before each analysis, the column is equilibrated at 30° C. in a 20 mM Tris/HCl buffer, pH 7.5, at a flow rate of 1.5 ml/min. The sample to be analysed, containing the viral particles, is injected into the column. To obtain maximum resolution, the quantity of particles injected should be less than or equal to $2 \times 10^{12}$ particles/ml of support. The volume injected has no substantial influence on the separation of the species, at least for an injected volume of less than or equal to 50 ml per ml of gel. After the injection, the column is rinsed with 5 volumes of the same buffer, and the bound species are eluted with a linear gradient of 0 to 1 M NaCl in the 20 mM Tris/HCl buffer, pH 7.5, over 30 column volumes. At the end of the gradient, the column is washed with 2 column volumes of 0.5 N sodium hydroxide before reequilibration for the next analysis.

A standard curve at 260 nm is constructed with a preparation of adenovirus particles purified either in a CsCl gradient, or by chromatography. This standard preparation was titrated beforehand for particles by its absorbance at 260 nm in a 0.1% SDS solution using the conversion factor of $1 \times 10^{10}$ particles per absorbance unit at 260 nm.

Figure 3:
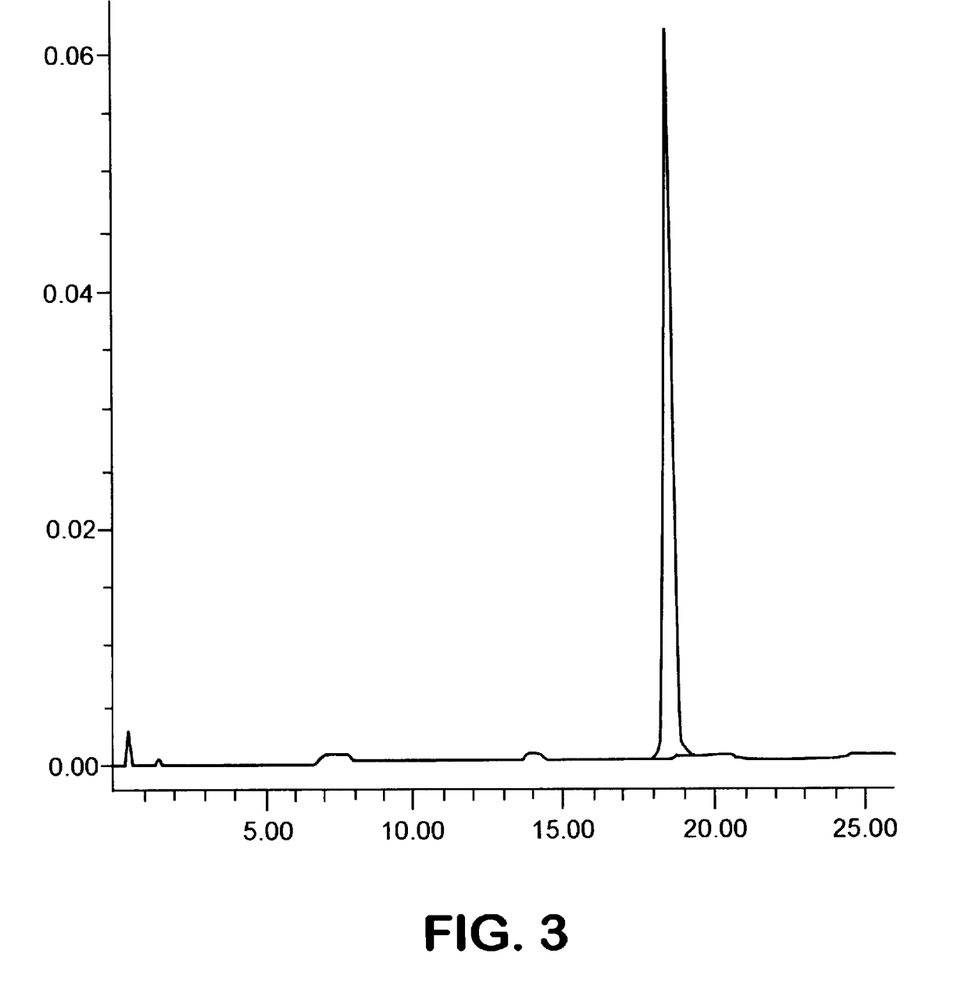
FIG. 3: Elution profile on Q SEPHAROSE XL for a preparation of purified adenovirus ($2\times10^{10}$ vp injected).

Under these conditions, the adenovirus is eluted at the retention time of about 18 min and has an absorbance ratio at 260 nm relative to 280 nm of 1.30±0.02 (see FIG. 3). The "Suitability" software for the chromatographic signal acquisition and processing unit Millennium Waters determines after each analysis, automatically, the value of N/m (calculated at half height) and the asymmetry (calculated at 10% of the height) of the peak. The value of N/m on the adenoviral peak is typically 35,000±3000 and the peak asymmetry factor is 1.05±0.05.

3-Preparative Method for the Purification of Adenoviruses by Anion-exchange Chromatography The adenovirus is purified from cultures of encapsidation cells 293 or PER.C6 (WO 97/00326). The virus is produced and harvested in supernatants after autolysis as described above. It is then filtered through a 0.45 μm membrane (HT Tuffryn or polysulphone) just before purification. Unless otherwise stated, the purification protocol is identical to the protocol used for the analytical separation of the viral particles which is described above, but with a different elution gradient. The elution is carried out with a 0.25 to 1 M NaCl gradient over 30 column volumes. The column volume is adjusted to the quantities of virus to be purified, considering a capacity of $1 \times 10^{12}$ particles per ml of chromatographic support. Likewise, the linear flow rate of the eluents is set at 300 cm/h.

EXAMPLES

Example 1

Comparison of Q SEPHAROSE XL Type Supports with the Q SEPHAROSE Fast Flow Support This example illustrates the specific properties of the Q SEPHAROSE XL type supports compared with the Q SEPHAROSE Fast Flow support.

Both supports consist of beads having an identical basic structure (6% cross-linked agarose), having the same particle size distribution (45–165 μm). They differ in the presence of flexible dextran arms carrying the Q type exchange groups for Q SEPHAROSE XL, whereas the same Q type groups are directly fixed to the agarose matrix in the case of Q SEPHAROSE FF.

A purified adenovirus preparation ($2 \times 10^{10}$ vp) is injected onto a Q SEPHAROSE XL column (1 ml of support) and eluted with an NaCl gradient as defined in paragraph 2 of the section Materials and Methods. The elution profile is presented in FIG. 3. Under the same conditions, an identical analysis is performed on a similar column filled with Q SEPHAROSE Fast Flow (FF) support. The elution profile is presented in FIG. 4. Comparison of the chromatographic performance is presented in the table below.

TABLE 1

Comparison of the chromatographic performance with the Q SEPHAROSE XL and Q SEPHAROSE FF supports

| Support | Efficiency (N/m) | Asymmetry |
|---|---|---|
| Q SEPHAROSE XL | 30,000 | 1.0 |
| Q SEPHAROSE FF | 5,000 | 1.0 |

Figure 4:
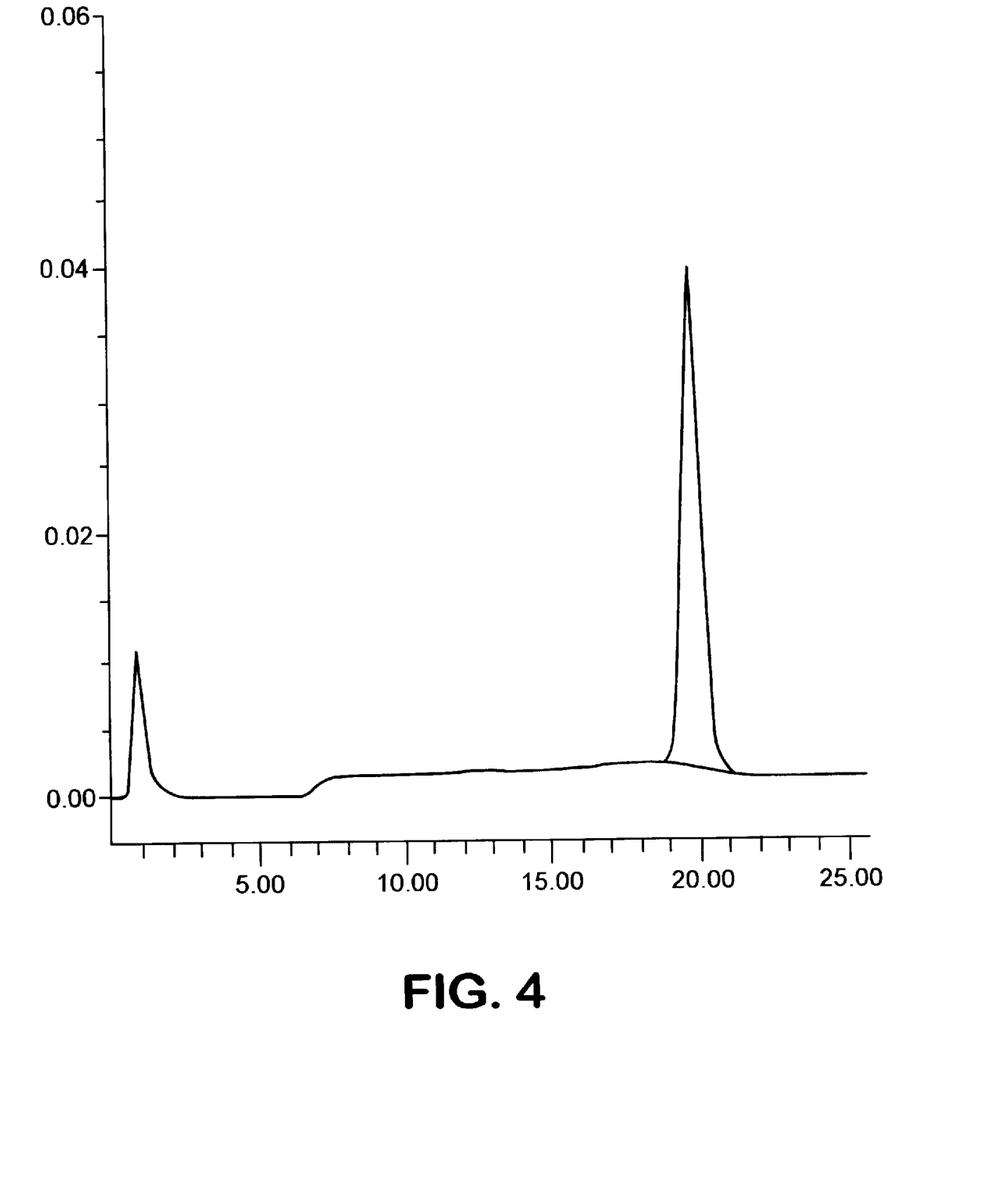
FIG. 4: Elution profile on Q SEPHAROSE Fast Flow for a preparation of purified adenovirus ($2\times10^{10}$ vp injected).

As shown in FIGS. 3 and 4, the virus retention time is similar in both cases (t=18 min for Q SEPHAROSE XL and t=20 mm for Q SEPHAROSE FF), but the Q SEPHAROSE XL support has a much higher efficiency than the Q SEPHAROSE FF support.

Figure 5:
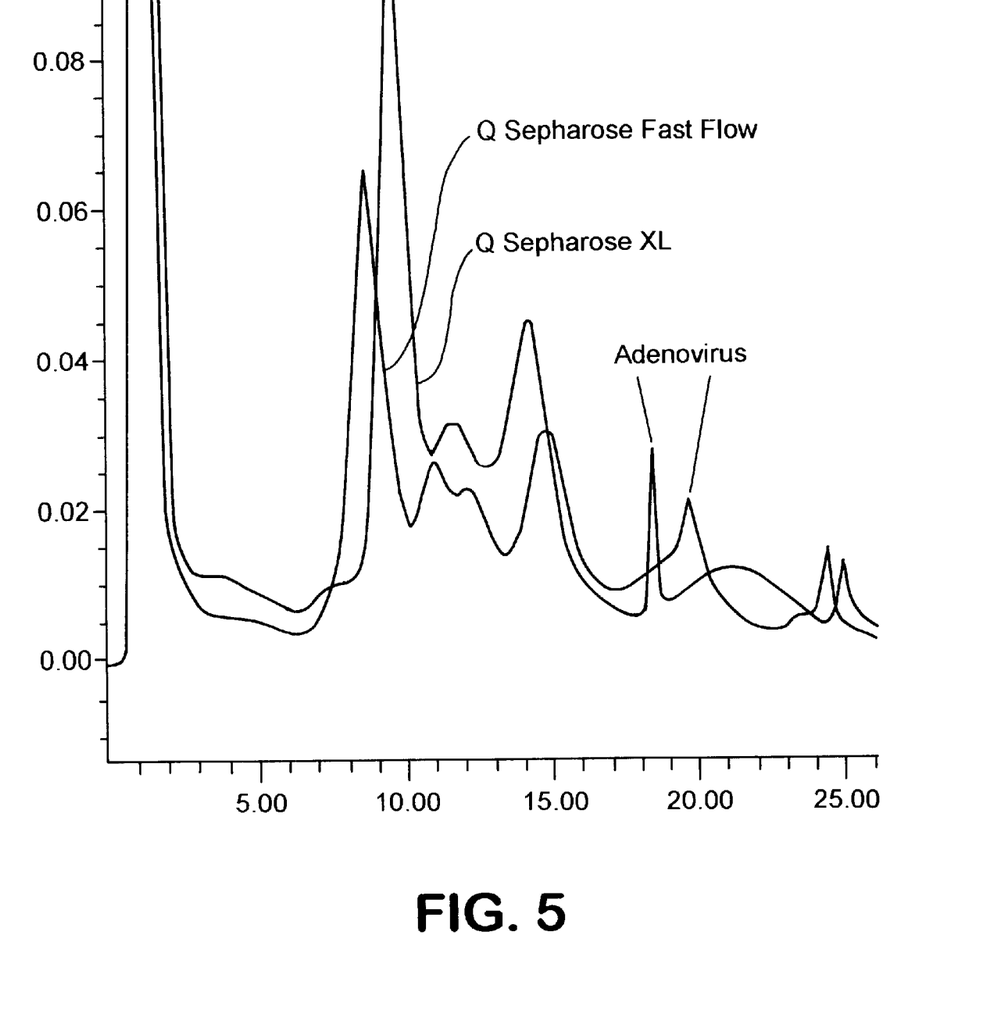
FIG. 5: Comparison of the elution profiles for a preparation of purified adenovirus on Q SEPHAROSE XL and Q SEPHAROSE Fast Flow.

In the same manner, analysis of a crude cellular extract containing $2 \times 10^9$ viral particles of adenovirus on both supports (FIG. 5) shows that only the Q SEPHAROSE XL support has an identified and quantifiable virus peak. On the other hand, the proteins present in the preparation are separated with an identical efficiency for both supports studied (FIG. 5).

These results indicate that the presence of the flexible arms carrying the exchange groups is a key component of this type of support. The presence of these flexible arms substantially contributes to the advantageous chromatographic performance of Q SEPHAROSE XL for the separation of adenoviruses.

Example 2

Comparison of the Q SEPHAROSE XL Type Supports with the Q SEPHAROSE HP Support

This example illustrates the specific properties of the Q SEPHAROSE XL type supports compared with the Q SEPHAROSE HP support.

The two supports consist of beads having an identical basic structure (6% cross-linked agarose). The Q SEPLIAROSE XL support has a bead size distribution ranging from 45 to 165 μm, centred on 90 μm. The particle size of the Q SEPHAROSE HP support is 34±10 μm. The particle size of the Q SEPHAROSE HP support is finer and a lot less dispersed than that of the Q SEPHAROSE XL support. The Q SEPHAROSE HP support should therefore have a much greater chromatographic performance than the performance of Q SEPHAROSE XL.

A purified adenovirus preparation ($2 \times 10^{10}$ vp) is injected on to a Q SEPHAROSE XL column (1 ml of support) and eluted with an NaCl gradient as defined in paragraph 2 of the section Materials and Methods. The elution profile is presented in FIG. 3. Under the same conditions, an identical analysis is carried out on a similar column filled with Q SEPHAROSE HP support. The elution profile obtained with the Q SEPHAROSE HP support is presented in FIG. 6.

Figure 6:
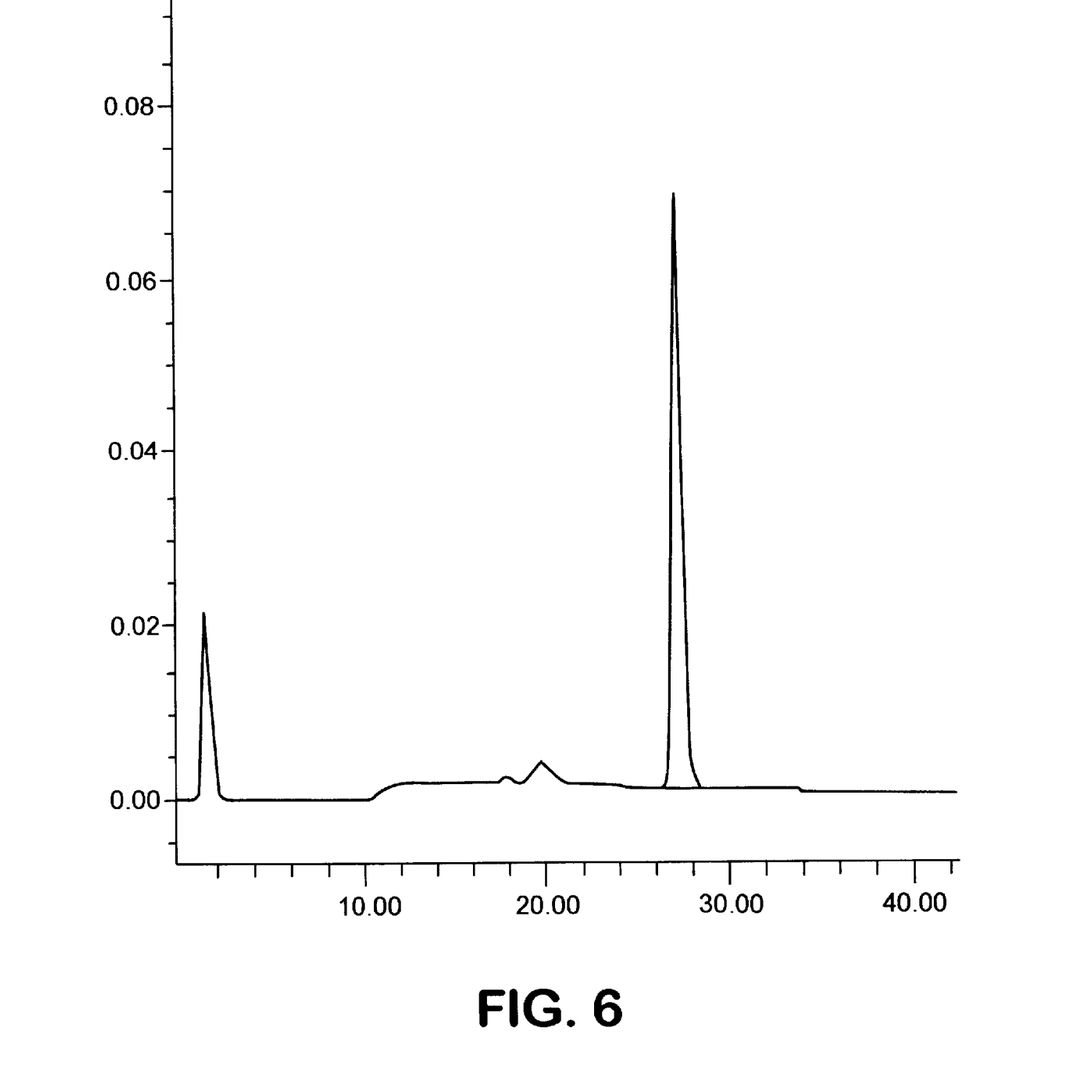
FIG. 6: Elution profile on Q SEPHAROSE HP for a preparation of purified adenovirus ($2\times10^{10}$ vp injected).

The results presented in FIG. 6 show that the Q SEPHAROSE HP support has a substantially lower efficiency (N/m, 15,000) than the Q SEPHAROSE XL support. Furthermore, the viral peak exhibits a substantial tailing on the Q SEPHAROSE HP support (asymmetry, 1.6), whereas it is strictly symmetrical on the Q SEPHAROSE XL support.

Unexpectedly, in spite of its finer particle size and its less dispersed particle size distribution, the Q SEPHAROSE HP support does not achieve the performance of the Q SEPHAROSE XL support for the separation of viral particles. It has, on the other hand, a far superior performance for the separation of proteins, as is indicated by the supplier (Amersham-Pharmacia Biotech) and as is confirmed under our experimental conditions with experiments for the separation of bovine albumin (table below).

TABLE 2

Comparison of the chromatographic performance with the Q SEPHAROSE XL and Q SEPHAROSE HP supports

| | Adenovirus | | Albumin |
|---|---|---|---|
| Support | Efficiency (N/m) | Asymmetry | Efficiency (N/m) |
| Q SEPHAROSE XL | 30,000 | 1.0 | 600 |
| Q SEPHAROSE HP | 15,000 | 1.6 | 4000 |

These results confirm that the presence of the flexible arms carrying the strong anion exchange groups is an essential component in the chromatographic performance of this type of support for the separation of viral particles. These results also indicate that another important parameter to be taken into account in defining the choice of the support is the particle size and in particular the size dispersion.

Example 3

Comparison of the Q SEPHAROSE XL Type Supports with the FRACTOGEL TMAE(S) and Source 15Q Supports This example illustrates the specific properties of the Q SEPHAROSE XL type supports compared with the FRACTOGEL TMAE(S) support and the Source 15Q support.

The three supports consist of beads of different structure and composition. The Q SEPHAROSE XL consists of 6% cross-linked agarose. The FRACTOGEL TMAE support is a cross-linked polymethacrylate resin and the Source 15Q support consists of polystyrene-divinylbenzene type resin beads. The particle size of the FRACTOGEL TMAE(S) (20–40 μm) and Source 15Q (15 μm) supports is considerably smaller and much less dispersed than that of the Q SEPHAROSE XL support (45–165 μm). Moreover, the three supports have the strong exchange groups. The latter are situated on flexible arms attached to the matrix in the case of FRACTOGEL TMAE(S) and Q SEPHAROSE XL, contrary to Source 15Q whose exchange groups are grafted directly onto the matrix.

A purified adenovirus preparation ($2 \times 10^{10}$ vp) is injected onto a Q SEPHAROSE XL column (1 ml of support) and eluted with an NaCl gradient as defined in paragraph 2 of the section Materials and Methods. The elution profile obtained is presented in FIG.3. Under the same conditions, an identical analysis is carried out on a similar column filled with Source 15Q support and another analysis is carried out on a column filled with FRACTOGEL TMAE(S) support.

Unexpectedly, in spite of its finer particle size, the FRACTOGEL TMAE(S) support does not achieve the performance of the Q SEPHAROSE XL support for the separation of adenoviruses. It exhibits, on the other hand, a much greater performance for the separation of proteins. Likewise, in spite of its very fine particle size and its virtually monodisperse particle size distribution, the Source 15Q support does not achieve the performance of the Q SEPHAROSE XL support for the separation of adenoviruses either.

TABLE 3

Comparison of the chromatographic performance with the Source 15Q, Q SEPHAROSE XL and FRACTOGEL TMAE(S) supports

| Support | Efficiency (N/m) | Asymmetry |
|---|---|---|
| Source 15Q | 20,000 | 1.2 |
| Q SEPHAROSE XL | 30,000 | 1.0 |
| FRACTOGEL TMAE(S) | 20,000 | 1.5 |

These results indicate that the presence of the flexible arms carrying the exchange groups is not the only factor responsible for the specific chromatographic performance of the Q SEPHAROSE XL support for the separation of adenoviruses. The chemical composition of these arms, their grafting density, the nature and porosity of the matrix on which the flexible arms are grafted are all the parameters which can influence the chromatographic performance of the support for the separation of viral particles.

Example 4

Detection and Quantification of Particles of Wild-type Adenoviruses of Various Serotypes This example illustrates a method of detecting and identifying particles of wild-type adenoviruses of various serotypes based on the use of the Q SEPHAROSE XL type chromatographic support.

The various wild-type adenoviruses were produced by infecting A549 cells cultured on DMEM medium and harvested after subjecting the cells to 3 freeze-thaw cycles. The preparation was then filtered through an Acrodisc membrane (type HT Tuffryn 0.45 µm; Gelman Sciences) before analysis.

The various preparations were then analysed by chromatography according to the protocol described in paragraph 2 of the section Materials and Methods. However, in the example presented, the analyses were carried out with a column having a volume which is slightly greater than 1 ml ($\approx$1.35 ml), which explains why the retention time for adenovirus 5 is greater (25.3 min) than the reference retention time (18 min) indicated in the section Materials and Methods.

TABLE 4

Chromatographic characterization of various wild-type adenoviruses

| ADENOVIRUS (SEROTYPE) | SUB-GROUP | TITRE (vp/ml) | Ratio (260/280) | $T_r$ (min) |
|---|---|---|---|---|
| 18 |   | $2.3 \times 10^9$ | 1.18 | 15.0 |
| 3 | B | $4.8 \times 10^{10}$ | 1.35 | 20.1 |
| 7 |   | $4.4 \times 10^{10}$ | 1.33 | 18.3 |
| 11 |   | $3.8 \times 10^{10}$ | 1.30 | 22.7 |
| 14 |   | $1.1 \times 10^{10}$ | 1.31 | 27.0 |
| 21 |   | $2.7 \times 10^{10}$ | 1.36 | 22.8 |
| 34 |   | $4.7 \times 10^{10}$ | 1.30 | 21.5 |
| 1 | C | $1.2 \times 10^{10}$ | 1.32 | 26.9 |
| 2 |   | $2.3 \times 10^{10}$ | 1.33 | 26.9 |
| 5 |   | $6.6 \times 10^{10}$ | 1.33 | 25.3 |
| 6 |   | $6.6 \times 10^{10}$ | 1.38 | 22.3 |
| 13 | D | $4.6 \times 10^{10}$ | 1.55 | 17.0 |
| 20 |   | $8.5 \times 10^{10}$ | 1.32 | 22.1 |
| 4 | E | $3.9 \times 10^{10}$ | 1.31 | 20.1 |
| 36 |   | $2.9 \times 10^{10}$ | 1.37 | 22.4 |

This example shows that the various adenoviruses not only have a variable retention time depending on the serotypes considered, but also a 260 nm/280 nm absorbance ratio which is characteristic of the serotype in question. The combination of these two criteria, which may be measured simultaneously during the one and same chromatographic analysis, therefore constitutes a rapid and reliable means of identifying the serotype of the adenovirus present in the chromatographic preparation.

A correlation was sought between the retention time for the virus on the column and the characteristics of the fibre and the hexon of the adenoviruses types 7, 3, 4, 5 and 2, for which the sequences are published (1998 J. Virol. (1998) 72 p. 7909 and Arch, Virol (1997) 142 p. 1307). No correlation is found from the sequence identity data for the head of the fibre, or even from the differences in the number of repeats of the β sheets in the stem of the fibre (see table below). On the other hand, and surprisingly, a correlation was found between the retention time for the virus and the sequence identity for the hexon (see table below). This correlation is in perfect agreement with the overall charge of the hexon at pH 7; this correlation shows that the rise in the charge of the hexon at pH 7 corresponds to an increase in the retention of the virus on the column. Slight differences may exist depending on the charge at pH 7 of the exposed L1 portion of the hexon, as indicated by the data obtained with the type 3 virus.

TABLE 5

Correlation between the virus retention time and the hexon sequence identity

| Adenovirus serotype | Sub-group | $T_r$ (min) | Fibre % identity head | Charge at pH 7 | Number of repeats stem | Hexon % identity hexon | Hexon pI | Hexon charge at pH 7 | L1 of hexon charge at pH 7 |
|---|---|---|---|---|---|---|---|---|---|
| 7 | B | 18.3 | 100 |   | 6 | 100 | 5.31 | −16.83 | −12.03 |
| 3 | B | 20.1 | 52 | −2.91 | 6 | 93.9 | 5.23 | −18.66 | −10.03 |
| 4 | E | 20.1 | 32 |   | 12 | 73.9 | 5.30 | −17.55 | −12.06 |
| 5 | C | 25.3 | 27 | −3.61 | 22 | 67.8 | 5.15 | −22.57 | −20.94 |
| 2 | C | 26.9 | 33 | −2.80 | 22 | 67.3 | 4.96 | −26.73 | −20.02 |

Example 5
Detection and Quantification of the Particles of Recombinant Adenoviruses During the Steps of Producing a Viral Stock This example illustrates the use of the Q SEPHAROSE XL type supports for the detection and quantification of particles of recombinant adenovirus $AV_{1.0}CMV.lacZ$ which are produced during the steps of transfection and amplification with various encapsidation cell lines (cells 293 or PER.C6).

This extremely rapid method of analysis provides, in a few minutes and using a culture supernatant, the titre of the adenovirus solution resulting from each step. This rapid and sensitive method makes it possible to optimize the amplification conditions of the next step which can then be carried out under defined and controlled MOI conditions.

This method of analysis was tested in order to verify the production of $AV_{1.0}CMV.lacZ$ recombinant adenoviruses during the steps of transfection and amplification on cells 293 or PER.C6.

The $AV_{1.0}CMV.lacZ$ adenovirus was produced after transfection of cells 293 or PER.C6 with the plasmid pXL2822 digested with PacI (Crouzet et al., Proc. Natl. Acad. Sci USA 94: 1414–1419, 1997) followed by infection of cells 293 or PER.C6, respectively, at a defined multiplicity of infection (MOI). The initial transfection was carried out with 5 to 10 micrograms of viral DNA obtained by digestion of the plasmid.

During the lysis of the cells, the virus was harvested by subjecting the cells to 3 freeze-thaw cycles. The preparations were then filtered through a 0.45 μm Acrodisc membrane (type HT Tuffryn) before analysis.

The various preparations were then analysed by chromatography according to the protocol described in paragraph 2 of the section Materials and Methods. The titre of the adenovirus solution is determined with reference to a standard curve prepared under the conditions described in paragraph 2 of the section Materials and Methods.

The results are presented in the table below.

TABLE 6

Detection and quantification of the $AV_{1.0}CMV.lacZ$ recombinant adenovirus particles obtained during the production of the viral stocks in two transcomplementation lines (293 or PER.C6)

| Cells | Virus | Step | Titre (vp/ml) | Total quantity (vp) |
|---|---|---|---|---|
| 293 | $AV_{1.0}CMV.lacZ$ | Transfection | $3.8 \times 10^8$ | $7.6 \times 10^9$ |
|  |  | Amplification I MOI 50 | $3.5 \times 10^{10}$ | $1.0 \times 10^{12}$ |
|  |  | Amplification II MOI 30 | $4.2 \times 10^{10}$ | $3.1 \times 10^{13}$ |
| PER.C6 | $AV_{1.0}CMV.lacZ$ | Transfection | $2.4 \times 10^8$ | $9.6 \times 10^9$ |
|  |  | Amplification I MOI 30 | $2.1 \times 10^{10}$ | $6.3 \times 10^{11}$ |
|  |  | Amplification II MOI 60 | $3.2 \times 10^{10}$ | $1.9 \times 10^{13}$ |

The total viral particles obtained were assayed in order to determine the concentration of infectious particles (pfu) and particles having the transgene activity (tdu). The term pfu ("plaque forming unit") corresponds to the infectious power of an adenovirus solution, and is determined by infecting an appropriate cell culture and measuring, generally after 15 days, the number of plaques of infected cells. These assays are based on biological methods and the values obtained may appear different depending on the conditions used (J. Virol. (1996) 70 p. 7498). Indeed, the formation of a plaque in a transcomplementation line does not necessarily describe the infectivity of the virus in other target cells (Biotechniques (1997) 22 p. 447). The results obtained are presented in the table below and the values obtained are in perfect agreement with the data in the literature (P. Yeh et al. J. Virol. (1996) 70 p. 559). Indeed, P. Yeh et al. describe AdRSVβGal viruses purified by caesium chloride gradient having tdu/pfu ratios of 0.49 to 0.68, which is very close to the results obtained below.

TABLE 7

Relationship between the concentration of infectious particles (pfu) and particles having the transgene activity (tdu)

| Cells | Virus | Titre (vp/ml) | Titre (pfu/ml) | vp/pfu | Titre (tdu/ml) | vp/tdu | tdu/pfu |
|---|---|---|---|---|---|---|---|
| 293 | $AV_{1.0}CMV.lacZ$ | $4.2 \times 10^{10}$ | $1.7 \times 10^9$ | 24 | $7.6 \times 10^8$ | 55 | 0.45 |
| PER.C6 | $AV_{1.0}CMV.lacZ$ | $3.2 \times 10^{10}$ | $1.3 \times 10^9$ | 26 | $7.4 \times 10^8$ | 43 | 0.57 |

Example 6
Detection and Quantification of Recombinant Adenovirus Particles Produced During the Steps of Transfection and Amplification on IGRP2 Cell This example illustrates the use of the Q SEPHAROSE XL type supports for the detection and quantification of $AV_{3.0}CMV.lacZ$ recombinant adenovirus particles produced during the steps of transfection and amplification on a cell IGRP2.

The adenovirus $AV_{3.0}CMV.lacZ$ was produced after transfection of IGRP2 encapsidation cells with the plasmid pXL3005 digested with PacI (the plasmid pXL3005 is derived from the plasmid pXL2811 described in (Crouzet et al., Proc. Natl. Acad. Sci USA 94: 1414–1419 1997) by exchange of the RSV promoter with the CMV promoter) followed by infection of IGRP2 cells (WO 96/22378) at a defined multiplicity of infection (MOI). During the lysis of the cells, the virus was harvested by subjecting the cells to 3 freeze-thaw cycles. The preparations were then filtered through a 0.45 μm Acrodisc membrane (type HT Tuffryn) before analysis.

The various preparations are then analysed by chromatography according to the protocol described in the section Materials and Methods. The results are presented in the table below.

TABLE 8

Detection and quantification of the
$AV_{3.0}CMV.lacz$ recombinant adenovirus particles obtained during the production of viral stocks

| Virus | Step | Titre (vp/ml) | Total quantity (vp) |
|---|---|---|---|
| $AV_{3.0}CMV.lacZ$ | transfection | $0.1 \times 10^{10}$ | $2.0 \times 10^{10}$ |
| | amplification I, MOI 100 | $1.54 \times 10^{10}$ | $1.4 \times 10^{12}$ |
| | amplification II, MOI 50 | $1.39 \times 10^{10}$ | $1.0 \times 10^{13}$ |

The total viral particles obtained were assayed in order to determine the concentration of particles having the transgene activity ($3.2 \times 10^8$ tdu/ml). A vp/tdu ratio of 43 is comparable to the vp/tdu ratio of 43 and 55 obtained in Example 5 and makes it possible to correlate the physical measurement $1.39 \times 10^{10}$ vp/ml of viral particles with the biological measurement of $3.2 \times 10^8$ tdu/ml of transduction units.

Example 7
Purification of the Virus by Chromatography on a Q SEPHAROSE XL Resin The starting material consists of either the culture lysate obtained by freezing-thawing the virus producing encapsidation cells, or the supernatant obtained after spontaneous lysis of the cells.

In the experiment reported in this example, 153 ml of an autolysate of culture of PER.C6 cells infected with the $AV_{1.0}CMV.LacZ$ virus containing $4.9 \times 10^{12}$ particles were injected onto a column of 5.8 ml of Q SEPHAROSE XL. The equilibration of the column and the elution of the virus were carried out at a flow rate of 300 cm/h with a 0.25 to 1 M NaCl gradient on 30 column volumes as described for the analytical separation of the virus in paragraph 2 of the section Materials and Methods. The viral peak (7.1 ml) was collected and then analysed by various techniques (IE-HPLC, SDS-PAGE) as described below. The fraction collected is analysed by high-performance liquid chromatography (HPLC) on a Resource Q column (1 ml) in the following chromatographic system: 10 μl of the fraction purified by chromatography as described above are injected onto a Resource Q15 column (1 ml of gel; Pharmacia) equilibrated in 100 mM Tris/HCl buffer, pH 8.0, containing 0.5 mM $MgCl_2$, (buffer B). After rinsing with 5 ml of buffer B, the adsorbed species are eluted with a linear gradient of 30 ml of NaCl (0 to 1 M) in buffer B at a flow rate of 1 ml/mm. The eluted species are detected at 260 nm. After the purification step on a Q SEPHAROSE XL column, the fraction collected has a purity $\geq$99% as viral particles (UV detection at 260 nm). The yield of purification of viral particles is 82%.

This HPLC analysis shows, furthermore, that the residual bovine serum albumin present in the starting lysate is completely removed during the preparative chromatography.

Electrophoretic analysis of the adenoviral fraction purified by chromatography is carried out on a polyacrylamide gel (4–20%) under denaturing conditions (SDS). The protein bands are then stained in silver nitrate. This analysis shows that the adenoviral preparation obtained by chromatography has a level of purity at least equal to that of the preparation conventionally obtained by ultracentrifugation and that it has no additional protein band which could bring about contamination of the preparation by nonadenoviral proteins.

The adenoviral preparation obtained by chromatography has an $A_{260\ nm}/A_{280\ nm}$ absorbance ratio equal to $1.30\pm0.05$. This value, which is identical to that obtained for the best preparations obtained by ultracentrifugation, indicates that the preparation is free of contaminating proteins or of contaminating nucleic acids.

Titration of the virus indeed shows the presence of infectious viral particles with a very satisfactory vp/pfu ratio (see table below) and the purified viral particles indeed have the expected infectious activity.

TABLE 9

Purification of $AV_{1.0}CMV.LacZ$ adenovirus on a Q SEPHAROSE XL support

| Step | Titre (vp/ml) | Titre (pfu/ml) | vp/pfu | Cumulative yield in vp (%) |
|---|---|---|---|---|
| Before Purification | $3.2 \times 10^{10}$ | $0.13 \times 10^{10}$ | 25 | — |
| Chromatographic Fraction | $56 \times 10^{10}$ | $1.6 \times 10^{10}$ | 34 | 81 |
| Product Formulated | $93 \times 10^{10}$ | $3.7 \times 10^{10}$ | 25 | 74 |

The method described in this example therefore makes it possible to purify adenoviral particles, without affecting their infectious power, directly from a lysate of encapsidation cells, with no prior treatment (ultrafiltration for example or treatment with a nuclease) of the material to be purified.

What is claimed is:

1. A method of separating viral particles from a biological medium selected from the group consisting of a supernatant of encapsidation cells producing the virus particles and a lysate of encapsidation cells producing the viral particles, the method comprising contacting the biological medium with a support comprising a cross-linked agarose matrix and ion-exchange groups bound to the cross-linked agarose matrix by a flexible arm, such that contact between the biological medium and the support chromatographically separates the viral particles from the biological medium.

2. The method according to claim 1, wherein the cross-linked agarose matrix has a particle size of between about 40 and 200 μm.

3. The method according to claim 2, wherein the cross-linked agarose matrix has a particle size of between 45 and 165 μm with a mean particle size of 90 μm.

4. The method according to claim 2, wherein 95% of the particles of the cross-linked agarose matrix have a diameter of between 0.1 and 10 times the mean diameter of the particles.

5. The method according to claim 1, wherein th flexible arm is a hydrophilic arm comprising a synthetic polymer or a natural polymer.

6. The method according to claim 5, wherein the hydrophilic arm is selected from the group consisting of a polyvinyl alcohol, a polyacrylamide, a polymethacrylamide, and a polyvinyl ether.

7. The method according to claim 5, wherein the hydrophilic arm is a polysaccharide selected from the group consisting of starch, cellulose, dextran and agarose.

8. The method according to claim 5, wherein the flexible arm has a degree of polymerization of about 30 monomeric units.

9. The method according to claim 8, wherein the flexible arm comprises a dextran having a mean molecular weight of about 5000 Da.

10. The method according to claim 1, wherein the ion-exchange group is an anion-exchange group.

11. The method according to claim 10, wherein the anion-exchange group is a quaternary amine.

12. The method according to claim 1, wherein the support comprises a cross-linked 6% agarose matrix with quaternary amine groups covalently attached to the matrix by way of flexible, hydrophilic dextran arms having a mean molecular weight of about 5000 Da, wherein the matrix has a particle size of between 45 and 165 μm and a mean particle size of 90 μm.

13. A method of quantifying adenoviruses in a supernatant or lysate of an adenovirus encapsidation culture, comprising the steps of:

contacting the supernatant or lysate with a support in order to chromatographically separate the adenoviruses from the supernatant or lysate, measuring the absorbance of the adenoviruses separated from the supernatant or lysate, and calculating from the measured absorbance the amount or concentration of the adenoviruses separated from the supernatant or lysate; wherein the support comprises a cross-linked 6% agarose matrix with quaternary amine groups covalently attached to the matrix by way of flexible, hydrophilic dextran arms having a mean molecular weight of about 5000 Da, wherein the matrix has a particle size of between 45 and 165 μm and a mean particle size of 90 μm.

14. The method according to claim 4, wherein 95% of the particles of the cross-linked agarose matrix have a diameter of between 0.3 and 3 times the mean diameter of the particles.

* * * * *